(12) United States Patent
Nelson et al.

(10) Patent No.: US 6,240,767 B1
(45) Date of Patent: *Jun. 5, 2001

(54) ETHYLENE MONITORING AND CONTROL SYSTEM

(76) Inventors: Bruce N. Nelson, 134 Eliot Ave., West Newton, MA (US) 02465; Roy V. Richard, II, 35 Pitts St., Natick, MA (US) 02760; James A. Kane, 3 Maple St., Norfolk, MA (US) 02056

( * ) Notice: Subject to any disclaimer, the term of this patent is extended or adjusted under 35 U.S.C. 154(b) by 0 days.

This patent is subject to a terminal disclaimer.

(21) Appl. No.: 09/523,254

(22) Filed: Mar. 10, 2000

Related U.S. Application Data

(63) Continuation of application No. 09/174,515, filed on Oct. 16, 1998, now Pat. No. 6,105,416.

(51) Int. Cl.[7] .................................................. G01N 21/24
(52) U.S. Cl. .............................. 73/23.2; 422/78; 436/135
(58) Field of Search ................................ 73/23.2, 863.55, 73/61.41, 31.02, 863.56; 436/135; 422/78; 250/361 C

(56) References Cited

U.S. PATENT DOCUMENTS

| | | |
|---|---|---|
| 3,710,107 | 1/1973 | Warren et al. . |
| 3,848,128 | 11/1974 | McMillan, Jr. .................. 250/361 C |
| 4,113,434 | 9/1978 | Tanaka et al. . |
| 4,140,487 | 2/1979 | Garlen et al. . |
| 4,193,963 | 3/1980 | Bruening et al. . |
| 4,393,304 | 7/1983 | Ishida et al. . |
| 5,152,963 | 10/1992 | Wreyford . |

FOREIGN PATENT DOCUMENTS

| | | |
|---|---|---|
| 4412343 A1 | 10/1994 | (DE) . |
| 0467307 A2 | 1/1992 | (EP) . |
| 08062130 | 3/1996 | (JP) . |
| WO 86/01296 | 2/1986 | (WO) . |
| WO 97/15822 | 5/1997 | (WO) . |

OTHER PUBLICATIONS

* Finlayson et al., "Low–Pressure Gas–Phase Ozone–Olefin Reactions. Chemiluminescence, Kinetics and Mechanisms", Journal of the American Chemical Society/96:17/, Aug. 21, 1974, pp. 5356–5367.
* Toby, "Chemiluminescence in the Reactions of Ozone", Chem. Rev. 84, 1984, pp. 227–285.
International Search Report dated Feb. 24, 2000.

*Primary Examiner*—Hezron Williams
*Assistant Examiner*—Jay I. Politzer
(74) *Attorney, Agent, or Firm*—Wolf, Greenfield & Sacks, P.C.; James H. Morris

(57) ABSTRACT

A system that can accurately monitor and control low concentrations of ethylene gas includes a test chamber configured to receive sample gas potentially containing an ethylene concentration and ozone, a detector configured to receive light produced during a reaction between the ethylene and ozone and to produce signals related thereto, and a computer connected to the detector to process the signals to determine therefrom a value of the concentration of ethylene in the sample gas. The supply for the system can include a four way valve configured to receive pressurized gas at one input and a test chamber. A piston is journaled in the test chamber with a drive end disposed in a drive chamber and a reaction end defining with walls of the test chamber a variable volume reaction chamber. The drive end of the piston is pneumatically connected to two ports of the four way valve to provide motive force to the piston. A manifold is connected to the variable volume reaction chamber, and is configured to receive sample gasses from at least one of a plurality of ports connectable to degreening rooms and to supply the sample gas to the reactive chamber for reaction with ozone. The apparatus can be used to monitor and control the ethylene concentration in multiple degreening rooms.

50 Claims, 6 Drawing Sheets

ETHYLENE MONITORING AND CONTROL SYSTEM

RELATED APPLICATIONS

This application is a continuation of U.S. application Ser. No. 09/174,515, filed Oct. 16, 1998, now U.S. Pat. No. 6,105,416.

U.S. GOVERNMENT RIGHTS IN THE INVENTION

This invention was made with Government support under Contract No. NAS 10-12003 awarded by NASA. The Government has certain rights in this invention.

BACKGROUND OF THE INVENTION

1. Field of The Invention

The present invention relates generally to system for monitoring and controlling low concentrations of reactive gasses and, more particularly, to a system for monitoring and controlling concentrations of ethylene gas.

2. Related Art

Perishable produce such as fruit, vegetables and cut flowers, must be consumed while fresh. To facilitate this, an elaborate distribution system has been developed to deploy rapidly harvested produce into supermarkets, restaurants, and other food stores. Produce that is not timely consumed must be destroyed or otherwise discarded. Optimal flow of produce through this distribution chain is important to minimize the amount of produce that must be discarded.

It is well known that the rate at which the produce ages may be controlled by controlling the concentration of ethylene in the atmosphere surrounding the produce. This is related to the fact that ethylene is a plant growth hormone. For many products, exposure to ethylene, even in low concentrations, speeds the aging process. If ethylene concentration levels are not controlled and rise above unacceptable levels, premature ripening or decay of the produce can occur, which may require the produce to be discarded before it is able to be sold.

It has been found that reducing the concentration of ethylene is important during transportation and storage of produce that naturally emits ethylene gas. For example, ventillating to remove excess ethylene has been found to reduce the rate of decay for many fruits and vegetables and is also particularly useful for maintaining the robustness of cut flowers, such as tulips, imported into the United States from Holland.

It is sometimes financially advantageous to pick oranges while still green and cause the peel to change color subsequent to harvesting. As is well known, exposing a green colored orange to a low concentration of ethylene gas over a long period of time (24–72 hours) causes the chlorophyll in the orange peel to break down, thus causing the orange peel to change color. This process will be referred to herein as "degreening."

Ethylene concentration between about 5 to 10 parts per million (ppm) affect the chlorophyll in the peel without penetrating into the fruit itself. Higher concentrations of ethylene, above about 10–15 ppm, however, have been found to cause the peel to break down and may cause the onset of mold in the peel. When this happens, the entire batch of fruit frequently must be discarded. By contrast, an insufficient amount of ethylene, below about 5 ppm, will delay the degreening process, thus inhibiting distribution of the current batch of fruit as well as batches of fruit waiting to enter the degreening rooms. Accordingly, controlling the concentration of ethylene during the degreening process is critical.

Controlling the concentration of ethylene has yet another use. Since ethylene is a plant growth hormone, increasing the concentration of ethylene may speed the ripening process for certain types of products. For example, it has been found that exposing tomatoes and bananas to ethylene in a concentration of about 100 ppm for a period of 12–24 hours will speed the ripening process for these products. Typically, a stepped process is used whereby the concentration is varied over time. Likewise, it is thus envisioned that controlled levels of ethylene gas could be used to stimulate plant production in outer space, should this ever become a reality.

Thus, monitoring and controlling the concentration of ethylene is important in many situations, especially during the production, transportation and storage of produce, during degreening of oranges, while ripening tomatoes and bananas and, potentially, in connection with growing plants in a controlled environment such as outer space. Unfortunately, detecting accurately ethylene concentrations, especially at the very low levels associated with degreening, is not trivial. Accordingly, there is a need for a system that can accurately monitor and control low concentrations of ethylene gas.

SUMMARY OF THE INVENTION

The present invention is a system that can accurately monitor and control low concentrations of ethylene gas. In one embodiment, a method includes reacting ozone and ethylene gas, detecting light produced by the reaction, and processing the detected light to determine a concentration of the ethylene gas. The method may also include controlling the concentration of the ethylene gas.

In another embodiment, an apparatus includes a test chamber configured to receive sample gas potentially containing an ethylene concentration and ozone, a light detector configured to receive light produced during a reaction between the ethylene and ozone and to produce signals related thereto, and a processor connected to the detector to process the signals to determine therefrom a value of the concentration of ethylene in the sample gas. The processor may be a general purpose computer running software configured to process the signals or a programmable logic controller.

In another embodiment, a supply for a testing device includes a four way valve configured to receive pressurized gas at one input and a test chamber having a piston journaled therein. A drive end of the piston is disposed in a drive chamber and a reaction end of the piston defines, with walls of the test chamber, a variable volume reaction chamber. The drive end of the piston is pneumatically connected to two ports of the four way valve to provide motive force to the piston. A manifold is connected to the variable volume reaction chamber, and is configured to receive sample gasses from at least one of a plurality of ports.

The supply may optionally contain a number of additional features, such as a vacuum pump connected to a port of the manifold, an ozone generator coupled to the variable volume reaction chamber to supply ozone to the variable volume reaction chamber, and a light detector such as a photo multiplier tube attached to the variable volume reaction chamber to receive light produced by a reaction between the sample gas and the ozone gas in the variable volume reaction chamber.

A computer may be configured to receive data indicative of light produced by the reaction from the light detector and to output information indicative of the concentration of ethylene gas in the sample gas. The computer may optionally be configured to receive data indicative of light produced by the reaction from the photo multiplier tube and to control the concentration of ethylene gas in an environment from which the sample gas was drawn. Control may be accomplished by injecting additional ethylene gas, e.g., by opening a supply valve, by maintaining the level of ethylene by regulating the flow of ethylene into the room or by decreasing the level of ethylene in the room by a combination of regulating the flow of ethylene into the room and ventilating the room.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

Figure 1:
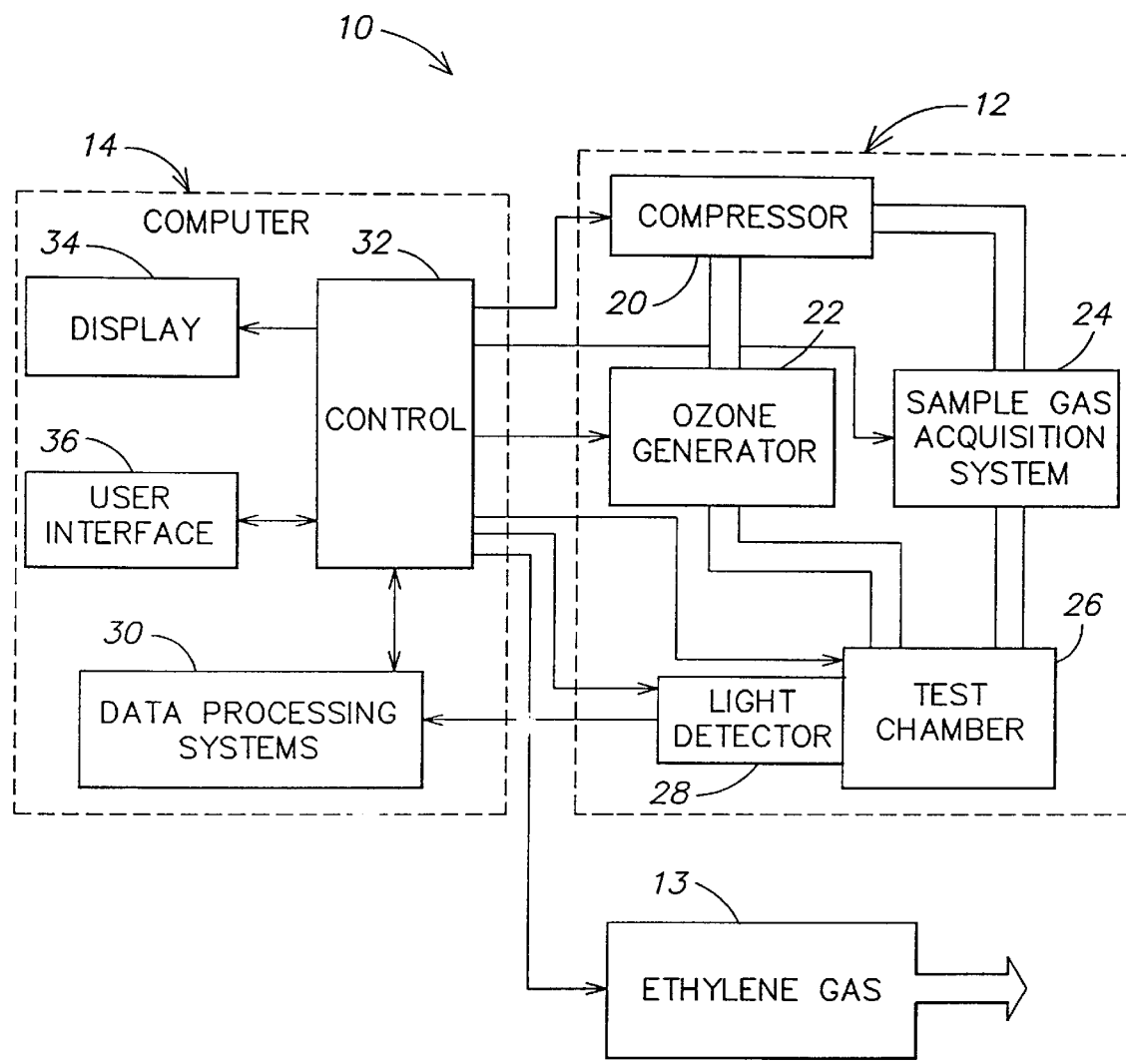
FIG. 1 is a functional block diagram of an ethylene monitoring and control apparatus of one embodiment of the present invention.

This invention is concerned with a system that can monitor and control low concentrations of ethylene gas accurately. Specifically, we have discovered that the chemilluminescent reaction between ethylene and ozone can be used to monitor and control accurately low concentrations of ethylene gas. This is useful, for example, in the degreening process and during the transportation and storage of produce.

The chemistry involved in the reaction between ethylene and ozone is well documented, and known in the art. Two exemplary articles on chemiluminescence include Toby, CHEMILUMINESCENCE IN THE REACTIONS OF OZONE, 84 Chem. Rev. 227–285 (1985), and Finlayson, et al. LOW PRESSURE GAS-PHASE OZONE-OLEFIN REACTIONS. CHEMILUMINESCENCE, KINETICS, AND MECHANISMS, J. Am. Chem. Soc. 96, 5356 (1974), the content of each of which is hereby incorporated by reference.

Briefly, the reaction between ozone and ethylene involves the formation of an intermediate product and its subsequent decomposition to form electronically excited formaldehyde, and electronically and vibrationally excited hydroxyl radicals. Photo-emissions from the decay of these excited state products to their ground states occur in the ultra-violet (electronically excited hydroxyl radical), the infrared (vibrationally excited hydroxyl radical) and visible (electronically excited formaldehyde) portions of the spectrum. Presently, the visible portion of the spectrum is deemed to be the easiest to use and thus has been selected as the primary vehicle for determining the concentration of ethylene present in the test gas. The other portions of the spectrum could, of course, also be used alone or in combination with detection in the visible portion of the spectrum to detect the concentration of ethylene.

In one embodiment of this invention, ozone is injected into a test chamber filled with a sample of gas containing ethylene (the test gas). The ozone reacts with the ethylene in the test chamber and light produced by the chemiluminescent reaction is detected. The term "light" will be used generically to refer to electromagnetic radiation and is not limited to electromagnetic radiation in the visible portion of the spectrum. The quantity of light is used to determine the concentration of ethylene gas in the test gas. If the concentration is found to be above or below a particular range of user determined values, the system can cause an alarm to be issued. Optionally, the system may also control automatically the environment to reduce or increase the level of ethylene gas. Where the system is monitoring and controlling simultaneously more than one source of test gas, the particular range of user determined values may be unique for each source of test gas.

One or both of the ozone and the test gas containing ethylene may be provided to the test chamber under pressure. Pressurizing the ozone has a number of benefits. First, pressurizing the ozone increases the number of ozone molecules available for reaction in the test chamber. This, in turn, causes a more complete and rapid reaction between the ethylene and ozone. Second, pressurizing the ozone makes it possible to use pressurized air instead of oxygen as the feed gas to the ozone generator. Using compressed air instead of oxygen is preferable because compressed air is less expensive than bottled oxygen, air creates less of an explosion hazard than bottled oxygen, and air does not need to be periodically replaced, as oxygen cylinders would typically need to be.

Likewise, pressurizing the test gas containing ethylene and providing the pressurized test gas to the test chamber increases the number of ethylene molecules available for reaction. This, in turn, can increase the signal to noise ratio by providing an increased number of reactions, and hence a brighter light source to be detected by the light detector.

As shown in FIG. 1, an ethylene detector 10 includes a test section 12 and a computer 14. The test section 12 contains the electrical and mechanical subsystems responsible for physical manipulation of gas streams. Additionally, the test section 12 may include data acquisition modules, such as pressure sensors, temperature sensors, photo multiplier tubes, and other appropriate sensors necessary or desirable for controlling the flow of the gas stream.

The computer 14 may be a general purpose computer running software configured to interact with components of the test section 12 or may be a special purpose computer such as a programmable logic controller (PLC). The computer 14 preferably is capable of receiving data from the components and/or sensors of the test section 12, processing the received data or otherwise using the data, and outputting information. The output information can be communicated to the user to enable the user to adjust manually the concentration of ethylene or can be used to control automatically the concentration of ethylene in the room. In either situation, the ethylene concentration may be controlled, for example, by adjusting the flow rate of ethylene gas into the room or energizing fans to ventilate the room.

The test section 12 in the embodiment illustrated in FIG. 1 includes a compressor 20 that provides a stream of compressed air to other components of the test section 12.

Although compressed air has been found to be sufficient, other sources of oxygen may also be used, for example compressed oxygen.

The compressed air is fed to an ozone generator 22 and a sample gas acquisition system 24 respectively. Sampled gas collected by the sample gas acquisition system 24 and ozone produced by the ozone generator 22 are mixed in the test chamber 26, where they are allowed to react. Light produced during the reaction is received by the light detector 28 and an electrical signal is provided from the light detector 28 to the computer 14. The electrical signal has features indicative of the amount of light produced during the reaction thus enabling the computer to determine the concentration of ethylene in the sampled gas.

The light detector may be any device capable of sensing light produced as a result of the reaction between ozone and ethylene. The Exact device will thus depend on a number of factors, including the intensity of the light produced during the reaction, the wavelength of interest in the produced light and the gain of the light detector. Exemplary light detectors include photo multiplier tubes (PMTs), avalanche photo diodes, CCDs, pin diodes, micro-channel plates, or any other light detector that can detect light produced in the reaction with the necessary sensitivity. In the preferred embodiment, a PMT is used to capture light produced during the reaction. More than one light detector may be used simultaneously to detect light produced in the same or different portions of the spectrum.

The light detecting device may detect light produced in one portion of the spectrum, for example in the visible spectrum, or may detect light produced in more than one portion of the spectrum. Where light is detected in more than one portion of the spectrum it may be necessary to use two or more light detectors, each of which is designed to detect a smaller subset of the spectrum. Detecting light in two portions of the spectrum, for example in the visible portion and the UV portion, may enable the computer 14 to differentiate the concentration of ethylene in the test gas from the concentration of other gases (such as NOx) in the test gas that also react with ozone.

The computer 14 contains many sub-systems, including a data processing system 30, a display 34, a user interface 36 and a control 32. The data processing system 30 receives signals from the test section 12 and processes the signals into usable form. The data processing system may contain one or more subsystems and/or software as is well known in the art.

A control section 32 is provided to control all aspects of the ethylene monitor 10. Specifically, in the illustrated embodiment, the control 32 controls the compressor 20, the ozone generator 22, the sample gas acquisition system 24, the test chamber 26, and the light detector 28 of the test section. Additionally, the control 32 controls the data processing system 30, the display 34 and the user interface 36. Control of these various components may be accomplished by communicating with the components directly or by communicating with associated electronic valves and other controls. Optionally, the control 32 can also control an ethylene source 13 to adjust automatically the ethylene concentration in the degreening room in response to the measured ethylene concentration.

Data from a number of sources may be taken into account while processing the data provided by the photo multiplier 28. Specifically, it may be desirable to provide the data processing system 30 with information relating to the pressure of the ozone, the amount of ozone injected into the test chamber, variables and commands input by the user via the user interface 36, the temperature of the gasses in the test chamber, and numerous other information that may affect computation of the ethylene concentration. Accordingly, control 32 provides the data processing system 30 with appropriate information to enable the data processing system to return appropriate values in an useable format. Reference test cycles interposed between data acquisition cycles may be used to calibrate the system to thereby enhance system accuracy.

A display is provided for displaying data indicative of the concentration of ethylene. The particular display format employed is a matter of design choice. It is currently envisioned that the display would, at a minimum, display the ethylene concentration in parts per million (ppm) or equivalent units for each active channel, i.e., each channel being sampled. The display may be physically associated within the computer 30 or may be remote from the components and connected to the computer over a network or other appropriate communication device. The display may include a general purpose display such as a computer monitor, or a special display such as a LCD display or LED display.

The user interface may be any appropriate device for entering information by a user. Exemplary interfaces include key boards, key pads, mice, touch screens, joy sticks, voice recognition software configured to enable the computer to receive commands orally, and any other possible user interface. Like the display, the user interface may be physically associated with the rest of the computer system 14 or may be physically located remotely from other components of the computer 14. A memory device may be provided to store permanently information communicated to the user or other information relating to the values derived by the data processing system.

Figure 2:
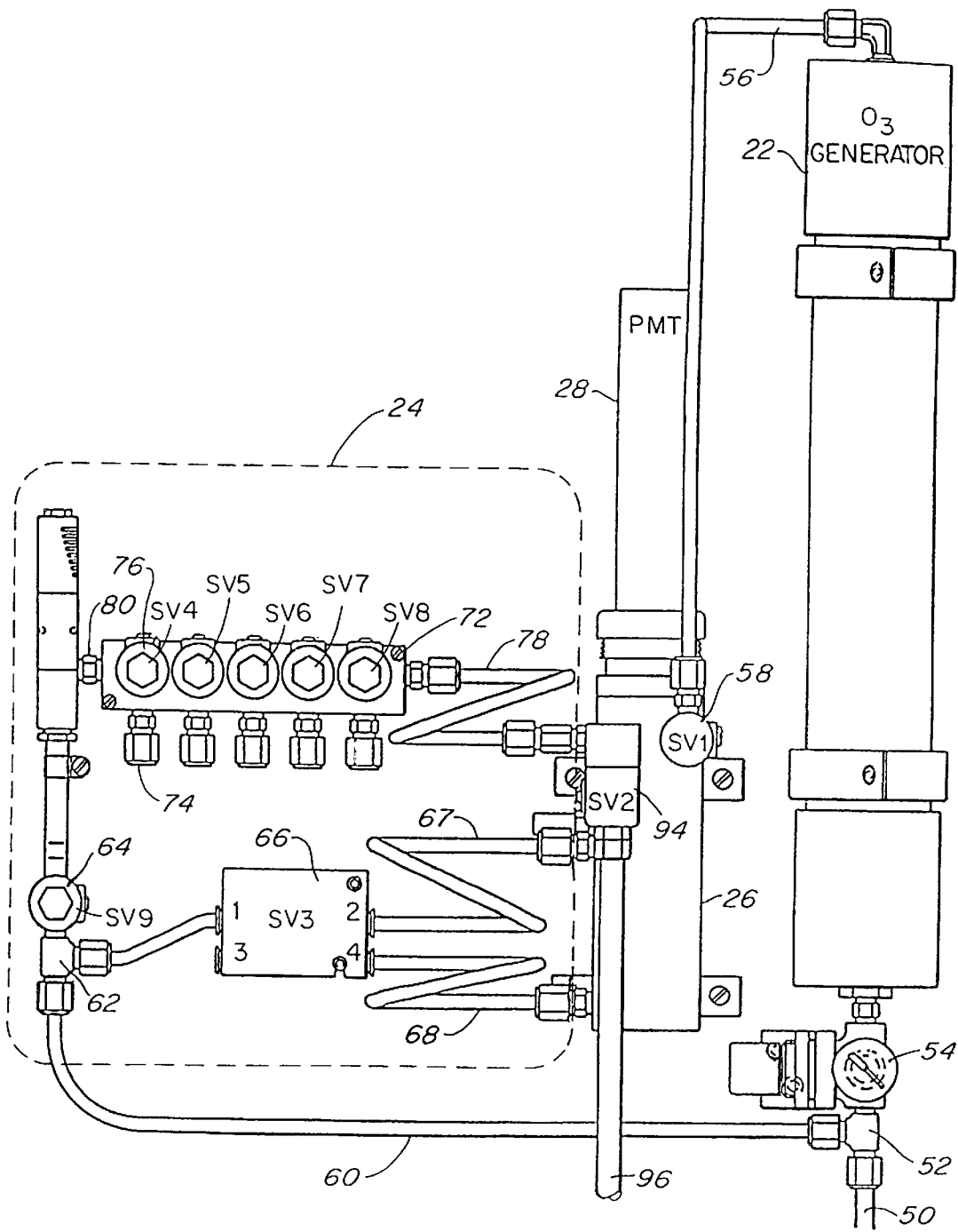
FIG. 2 is a schematic of the test section of the ethylene monitoring and control apparatus of FIG. 1.

FIG. 2 illustrates the test section 12 in greater detail. For simplicity, electrical interconnections have been omitted so that the flow of gas between various components is more easily understood. Providing electrical interconnections to the various components to electronically control the components is known and well within the level of skill in the art.

In FIG. 2, pressurized air enters via tube 50 at the lower right hand corner. The pressurized air flows through a tee 52 where the flow is split into two flows: one to supply oxygen to the ozone generator 22 and another to supply pressurized air for driving the sample gas acquisition system 24.

A pressure regulator 54 is interposed between tee 52 and ozone generator 22 to regulate the flow of pressurized air into the ozone generator 22. Ozone generator 22 is preferably a PZ II CARTRADGE (TM) ozone generator with ballast commercially available from PROZONE (TM). Since pressurized air is supplied to the ozone generator 22, the pressure of the gas exiting the ozone generator via tube 56 is also pressurized. Since this gas contains ozone, pressurized ozone is produced by the ozone generator 22. A first valve 58 controls injection of the pressurized ozone into the test chamber 26.

Pressurized air is supplied to the sample gas acquisition system 24 via tube 50, tee 52 and tube 60. The pressure of the air supply may be set at 80 psi or another appropriate value. Tube 60 is connected to a tee 62 that splits the flow of pressurized air to supply both a manifold vacuum pump 64 and a four way control valve 66. Tubes 68 and 67 connect the pressurized air to the test chamber 26 to control sampling of test gasses.

A manifold 72 has a plurality of inlet ports 74 controlled by valves 76. Although five inlet ports are illustrated, any number of ports could be used, depending on the requirements and capabilities of the system. The inlet ports 74 are connected to degreening rooms or other chambers potentially containing ethylene gas. The manifold 72 is connected to the test chamber 26 via tube 78.

Figure 3:
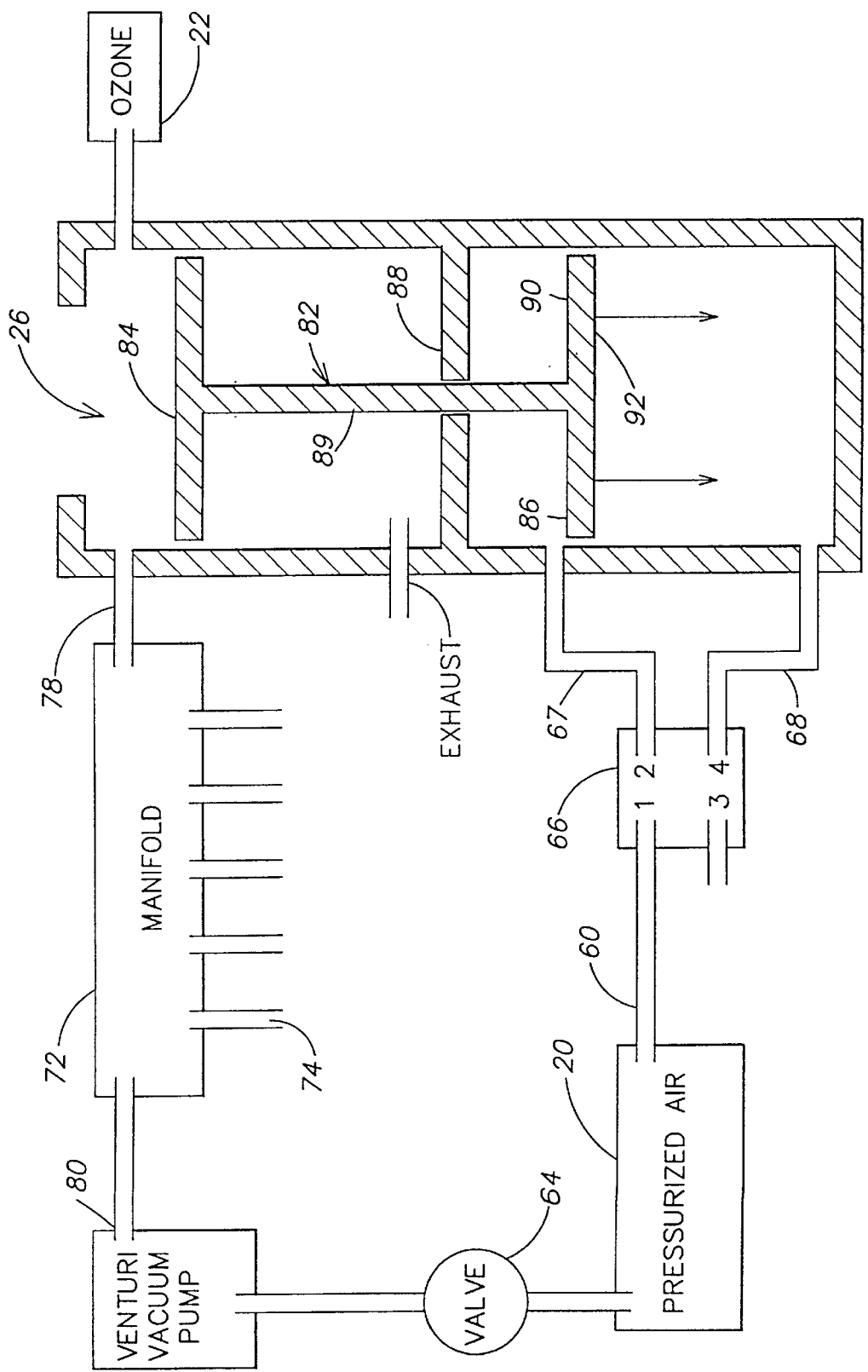
FIGS. 3 and 4 are schematics illustrating, in greater detail, operation of the test section and internal operation of the test chamber of FIG. 2.

Operation of the various components will now be explained more particularly with reference to FIGS. 3 and 4. As shown in FIG. 3, the test chamber 26 includes a piston 82 generally formed of a test gas cylinder head 84, a control gas cylinder head 86 and an interconnect 89 joining the test gas cylinder head 84 and the control gas cylinder head 86.

To sample gas from one of the inlet ports 74, the venturi vacuum pump 64 is turned on causing pressurized air to rush past aperture 80 in manifold 72. One of the valves 76 associated with an appropriate inlet port 74 is turned on. The partial vacuum caused by the venturi vacuum pump evacuates old gasses from the manifold and associated tubes, and causes sample gas to flow into the manifold and fill the manifold from the degreening room.

The sample gas contained in the manifold is then drawn into the test chamber by operating the sample drive four way valve 66. This operation is best illustrated in FIGS. 3 and 4. As shown in FIG. 3, to draw the sample gas into the test chamber 26, the four way control valve 66 connects pressurized air input to the four way valve at port number 1 to the tube 67 connected to port number 2. At the same time, the tube 68 connected to port number 4 is connected to port number 3, which is exhausted to the atmosphere. The pressurized air will thus flow into an area of the test chamber 26 between a bifurcating member 88 and an inside surface 90 of the control gas cylinder head 86, to cause the piston 82 to move in the direction of the arrows in FIG. 3 relative to the bifurcation 88. Since the control gas cylinder head 86 is connected to the test gas cylinder head 84, the test gas cylinder head 84 will also move, thus drawing test gas from the manifold 72, through tube 78 and into the test cylinder 26. Subsequently, ozone is injected into the test cylinder 26 to react with ethylene in the test gas. Note, that an exhaust is provided in the wall of the test chamber between the bifurcation 88 and the lower surface of the test gas cylinder head 84 to enable air to vent into and out of this portion of the test chamber as is necessary.

Figure 4:
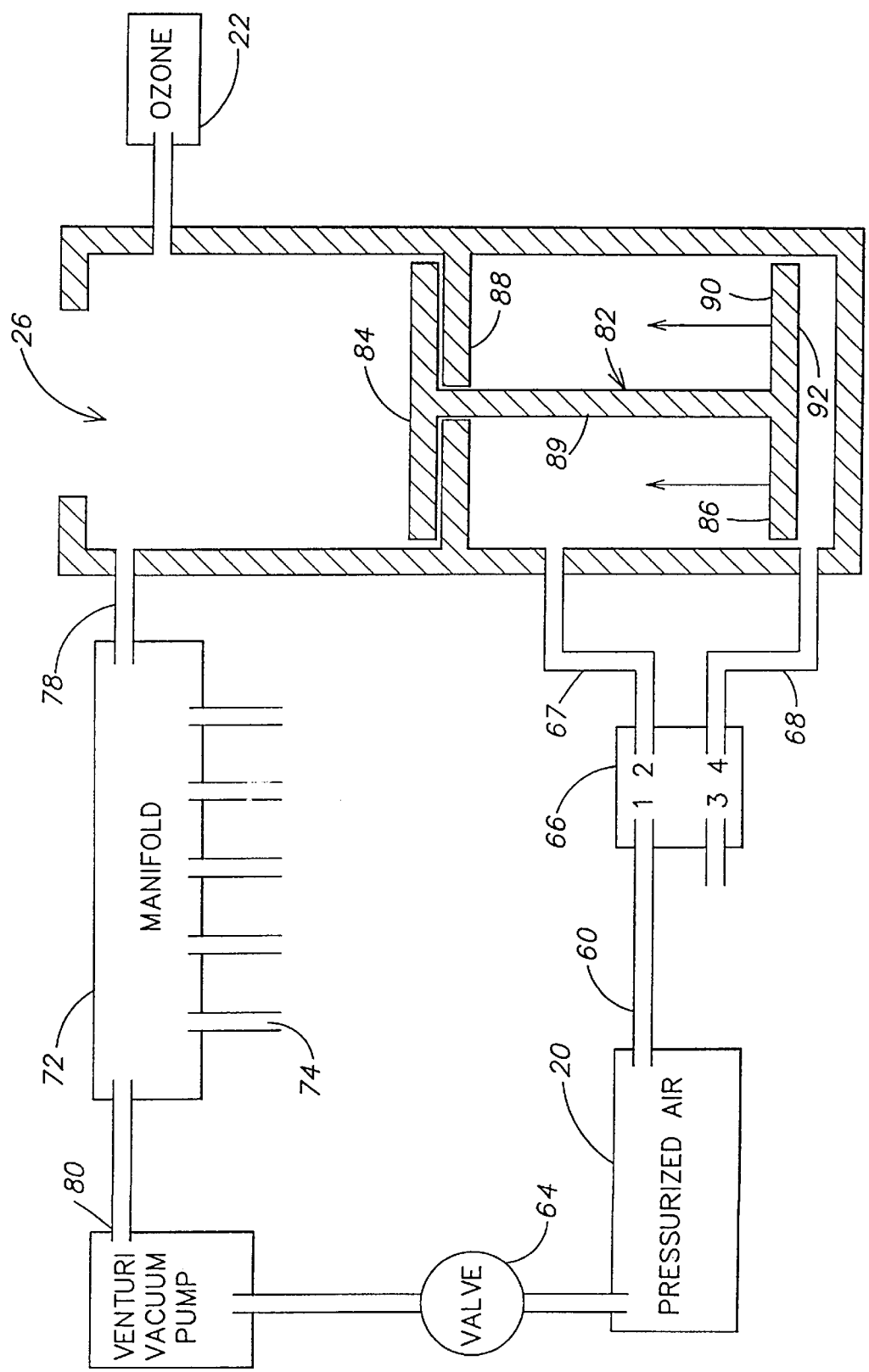

After the reaction has taken place, as illustrated in FIG. 4, the four way control valve 66 will be reconfigured so that pressurized air input at port number 1 will be connected to tube 68 connected to port number 4 and tube 67 connected to port number 2 will be connected to exhaust at port number 3. Thus, the pressurized air will press against the opposite surface 92 of the control gas cylinder head 86 to cause the piston 82 to move in the direction of the arrows in FIG. 4.

Just prior to movement of the piston 82 in the direction of the arrows in FIG. 4, an exhaust valve 94 is opened. Thus, movement of the test gas cylinder head 84 will cause the reacted gases in the test chamber to exit the test chamber via the exhaust valve 94 and exhaust tube 96, illustrated in FIG. 2, to complete one test gas cycle.

A reference measurement cycle may be performed to compensate for drift in any of the monitoring system's components. A reference measurement cycle includes injecting ozone gas into the test chamber without the presence of ethylene gas and detecting the light level produced in the absence of significant reaction. The light levels obtained during the reference measurement cycle can be used to adjust the zero of the system or otherwise to compensate for instrumentation induced errors in the detection system.

It is also possible to pressurize the test gas prior to injecting ozone into the test chamber 26. To do this, after the sample gas is drawn into the test chamber 26, a valve on the supply line 78 is closed to seal the test chamber 26. The four way control valve 66 is then used to direct pressurized air through tube 68 thereby causing the piston 82 to move up and compress the sample gas within test chamber 26. After the test gas has been compressed, the ozone is injected and the compressed ozone and ethylene in the compressed sample gas allowed to react. Pressurizing the sample gas should result in an increase in the rate of reaction between ethylene and ozone, as well as confine the reaction to a smaller volume. Accordingly, using pressurized sample gas as well as pressurized ozone should make it easier to detect light produced during the reaction.

To operate efficiently, seals must be provided between the walls of the test chamber 26 and edges of the control gas cylinder head 86 and edges of the test gas cylinder head 84. O-rings coated with grease that will not react with ozone may be used for this purpose. One exemplary grease for use in lubricating the O-ring is KRYTOX® grease, available from DuPont. KRYTOX® grease is made from a perfluropolyether (PFPE) based clear colorless fluorinated synthetic oil thickened with sub-micron (0.2 micron) particles of polytetrafluoroethylene (PTFE).

Likewise, to generate sufficient force to move the piston 82 within the test chamber 26, a seal must be formed between bifurcation 88 and interconnect 89. An O-ring coated with KRYTOX® is acceptable for this seal as well. However, since this seal would not be exposed to ozone under ordinary operating conditions, standard vacuum grease could be used in connection with this seal.

Figure 5:
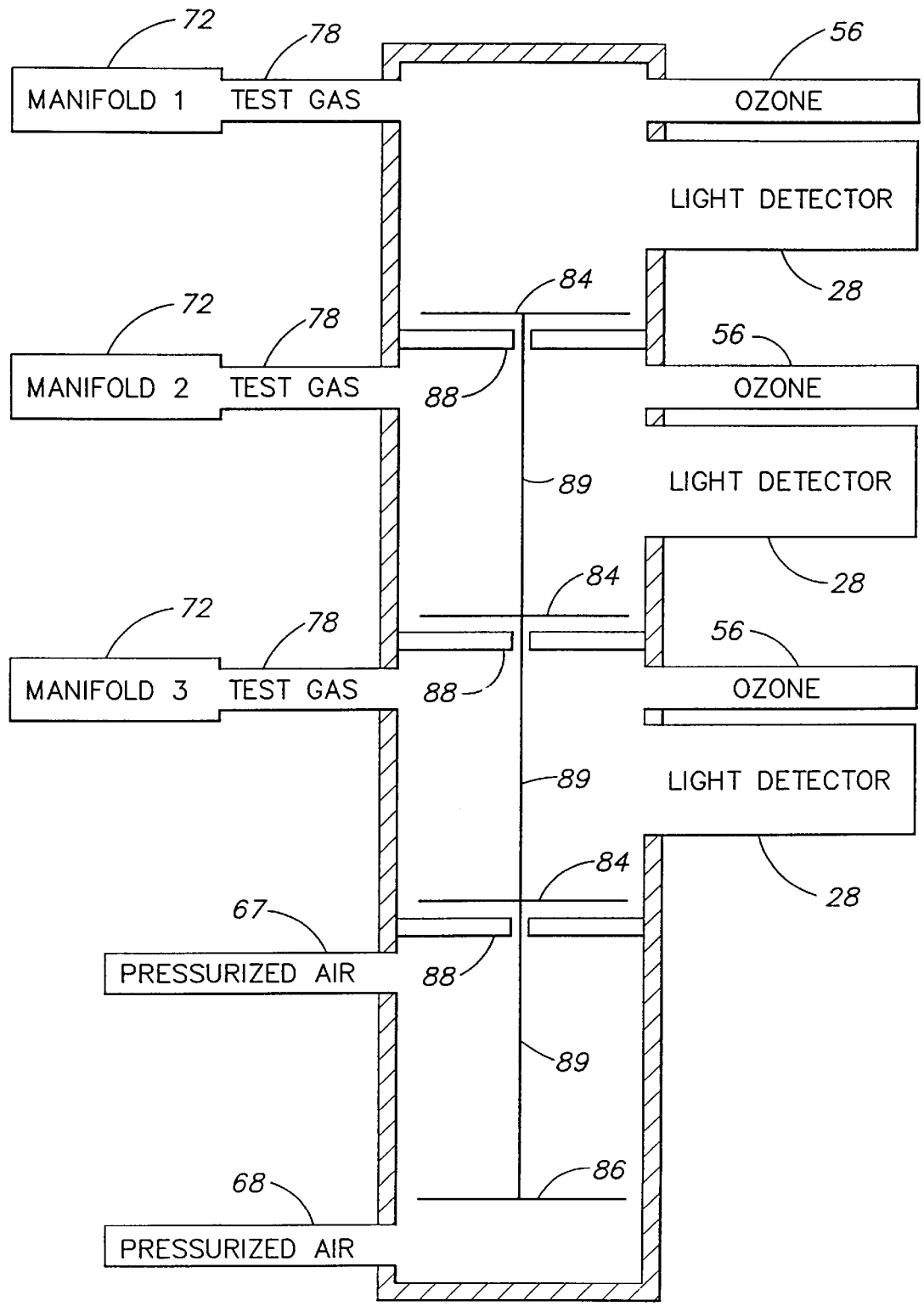
FIG. 5 is a schematic of an alternative embodiment of the test section of the ethylene monitoring and control apparatus of FIG. 1.

It should be understood that various changes and modifications of the embodiments shown in the drawings and described in the specification may be made within the spirit and scope of the present invention. For example, although pneumatic activation has been described as providing motive force to the piston 82, alternative systems could likewise be used, such as a solenoid or electric motor. Likewise, the various components forming the computer could be physically embodied in one computer system or could be physically separated and linked together using known protocols. Finally, as shown in FIG. 5, more than one test area may be provided in the same test chamber to facilitate simultaneous testing of more than one test gas.

Figure 6:
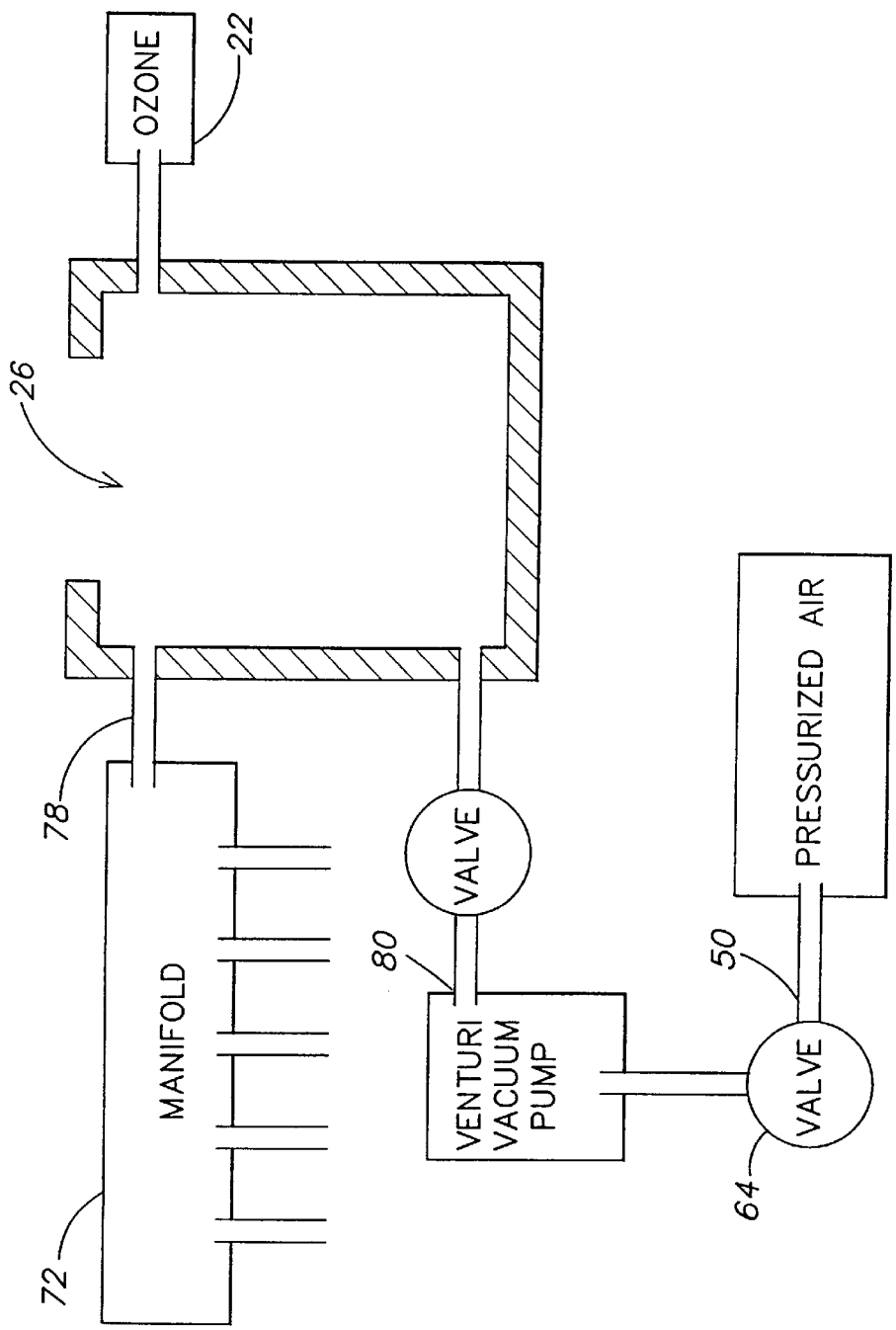
FIG. 6 is a schematic of an alternative embodiment of the test section of the ethylene monitoring and control apparatus of FIG. 1.

Numerous other test chambers could be used in addition to the above-described test chamber. For example, in addition to the piston-based variable volume test chamber, a variable volume test chamber formed from bellows or using a diaphragm could also be used. Likewise, the test chamber need not have a variable volume, but may instead be formed from a static volume. In a static volume system, the test gasses, exhaust gasses, ozone and other gasses could be injected into the test chamber under pressure or maybe drawn into the test chamber by generation of a partial vacuum. One exemplary way of creating a partial vacuum is to attach a venturi vacuum pump to the exhaust port of the test chamber, as shown in FIG. 6.

The present invention has been described as sensing the reaction between ethylene and ozone by sensing light produced in the reaction with a photo multiplier tube. Alternative embodiments may include detecting any difference in pressure or temperature resulting from the reaction, or by testing for the presence of reacted products produced during the reaction between ozone and ethylene.

Accordingly, it is intended that all matter contained in the above description and shown in the accompanying drawings be interpreted in an illustrative and not in a limiting sense.

The invention is limited only as defined in the following claims and the equivalents thereto.

What is claimed is:

1. A method, comprising the steps of:
   providing ozone from a first source at a first pressure and a test gas from a second source at a second pressure less than the first pressure, the test gas potentially containing ethylene;
   mixing the ozone with the test gas;
   reacting the ozone with any ethylene in the test gas;
   detecting light produced by the reaction to obtain a measured value;
   obtaining a reference value from the test chamber in the absence of the test gas;
   subtracting the reference value from the measured value; and
   determining a concentration of any ethylene in the test gas from the detected light.

2. The method of claim 1, wherein the test gas has been drawn from an atmosphere and the method further comprising the step of:
   controlling the concentration of ethylene gas in the atmosphere.

3. The method of claim 1, wherein the first pressure is higher than atmospheric pressure.

4. The method of claim 1, wherein the second pressure is approximately atmospheric pressure.

5. A method, comprising the steps of:
   obtaining a sample of test gas potentially containing ethylene;
   causing the sample of test gas to enter a test chamber;
   pressurizing the test gas;
   injecting ozone into the test chamber at a pressure higher than a pressure of the test gas;
   detecting a reaction between the ozone and any ethylene in the test gas to obtain a measured value;
   obtaining a reference value from the test chamber in the absence of the test gas; and
   subtracting the reference value from the measured value.

6. The method of claim 5, wherein the step of pressurizing the test gas occurs before the ozone is injected into the test chamber.

7. The method of claim 5, wherein the ozone is injected into the test chamber under pressure.

8. The method of claim 5, wherein the step of pressurizing the test gas occurs after the ozone is injected into the test chamber via pressurizing a mixture of the test gas and ozone.

9. The method of claim 5, further comprising the steps of:
   determining a result based at least in part on the detected reaction; and
   at least one of a step of increasing an ethylene concentration in the source of test gas if the determined concentration is too low and a step of decreasing the ethylene concentration in the source of test gas if the determined concentration is too high.

10. The method of claim 5, further comprising the step of:
    obtaining a reference value from the test chamber in the absence of the test gas for use in connection with the step of determining the concentration.

11. The method of claim 10, wherein the step of obtaining the reference value comprises the steps of:
    injecting ozone into the test chamber;
    producing electrical signals from sensors used to detect light; and
    processing the electrical signals to determine the reference value.

12. The method of claim 5, wherein the sample of test gas is a discrete sample of test gas.

13. The method of claim 5, wherein the step of pressurizing the test gas causes the pressure of the test gas to exceed one atmosphere pressure.

14. The method of claim 5, further comprising the step of isolating the sample of test gas in the test chamber from a source of the test gas.

15. A method, comprising the steps of:
    obtaining a sample of test gas potentially containing ethylene;
    causing the sample of test gas to enter a test chamber;
    injecting ozone having a pressure higher than a pressure of the test gas into the test chamber;
    allowing the ozone to react with any ethylene in the test gas;
    detecting light produced by the reaction to obtain a measured value;
    obtaining a reference value from the test chamber in the absence of the test gas;
    subtracting the reference value from the measured value;
    producing electrical signals based on the detected light; and
    processing the electrical signals to determine a concentration of the ethylene gas in the test gas.

16. The method of claim 15, further comprising a step of displaying an indicia of the determined concentration.

17. The method of claim 15, further comprising at least one of a step of increasing an ethylene concentration in the source of test gas if the determined concentration is too low and a step of decreasing the ethylene concentration in the source of test gas if the determined concentration is too high.

18. The method of claim 17, further comprising the steps of obtaining a second sample of test gas and injecting the second sample of test gas into the test chamber, after the step of producing the electrical signals.

19. The method of claim 15, further comprising the step of:
    compressing the sample prior to or concurrent with the step of allowing the ozone to react with the ethylene.

20. The method of claim 15,
    wherein the step of obtaining the reference value from the test chamber in the absence of the test gas is for use in connection with the step of determining the concentration to compensate for other sources of chemiluminescence.

21. The method of claim 20, wherein the step of obtaining the reference value comprises the steps of:
    injecting ozone into the test chamber;
    detecting light produced by reactions between the ozone and substances other than ethylene;
    producing electrical signals based on the detected light; and
    processing the electrical signals to determine the reference value.

22. The method of claim 20, wherein the test chamber is formed of non-inert material, and wherein the other source of chemiluminescence includes at least the non-inert material.

23. The method of claim 15, further comprising the step of:
    obtaining a reference value for use in connection with the step of determining the concentration, before the steps of obtaining a second sample of test gas and injecting the second sample of test gas into the test chamber.

24. The method of claim 15, further comprising the step of isolating the sample of test gas in the test chamber.

25. The method of claim 15, wherein the step of causing the sample of test gas to enter the test chamber is performed using a venturi pump in an exit opening in fluid communication with the test chamber.

26. The method of claim 15, further comprising the steps of compressing the sample to a compressed sample pressure, and wherein the pressure of the ozone is higher than the compressed sample pressure.

27. An apparatus, comprising:
a test chamber configured to receive from a first source a sample of test gas potentially containing an ethylene concentration and, from a second source, ozone having a pressure higher than a pressure of the test gas; and
a detector configured to receive light produced during a reaction between the ethylene and ozone and to produce signals related thereto to obtain a measured value, the detector also being configured to receive any light produced in obtaining a reference value of the test chamber in the absence of the test gas, the reference value to be subtracted from the measured value.

28. The apparatus of claim 27, a further comprising a general purpose computer containing software configured to receive the signals and process the signals to determine therefrom a value of the concentration of ethylene in the sample gas.

29. The apparatus of claim 27, further comprising a special purpose computer configured to receive the signals and process the signals to determine therefrom a value of the concentration of ethylene in the sample gas.

30. The apparatus of claim 27, wherein the test chamber is configured to receive a discrete sample of test gas.

31. The apparatus of claim 27, wherein the test chamber is constructed and arranged to receive sequential multiple discrete samples of test gas.

32. The apparatus of claim 27, wherein the test chamber is configured to receive the sample of test gas at superatmospheric pressure.

33. The apparatus of claim 27, wherein the test chamber is configured to receive the sample of test gas at approximately atmospheric pressure.

34. The apparatus of claim 33, wherein the test chamber is configured to receive the ozone gas at superatmospheric pressure.

35. The apparatus of claim 27, further comprising means for isolating the test chamber from a source of the test gas.

36. The apparatus of claim 27, further comprising a valve configured to isolate the test chamber from a source of the test gas.

37. The apparatus of claim 27, further comprising a venturi vacuum pump pneumatically connected to the test chamber.

38. An apparatus, comprising:
a test chamber configured to receive a sample of test gas potentially containing an ethylene concentration and ozone; and
a detector configured to receive light produced during a reaction between the ethylene and ozone and to produce signals related thereto to obtain a measured value, the detector also being confined to receive any light produced in obtaining a reference value of the test chamber in the absence of the test gas, the reference value to be subtracted from the measured value;
wherein the test chamber is constructed and arranged to receive sequential multiple discrete samples of pressurized ozone.

39. The apparatus of claim 38, further comprising a general purpose computer containing software configured to receive the signals and process the signals to determine therefrom a concentration of ethylene in the sample gas.

40. The apparatus of claim 38, further comprising a special purpose computer configured to receive the signals and process the signals to determine therefrom a concentration of ethylene in the sample gas.

41. The apparatus of claim 40, wherein the computer is a programmable logic controller.

42. The apparatus of claim 38, wherein the test chamber is a constant volume test chamber.

43. The apparatus of claim 42, further comprising a venturi vacuum pump pneumatically connected to the test chamber.

44. The apparatus of claim 38, further comprising a source of ozone to provide the ozone to the test chamber.

45. The apparatus of claim 44, wherein the source of ozone provides the ozone under pressure to the test chamber.

46. The apparatus of claim 45, wherein the source of ozone is an ozone generator configured to receive a supply of compressed air, convert at least a portion of the oxygen molecules in the compressed air into ozone, and supply the ozone under pressure to the test chamber.

47. The apparatus of claim 46, wherein the ozone generator is an UV type ozone generator.

48. The apparatus of claim 38, wherein the test chamber is configured to receive discrete samples of test gas under pressure. ease add the following claims.

49. The apparatus of claim 38, wherein the test chamber is constructed and arranged to contain discrete samples of test gas.

50. The apparatus of claim 49, wherein the test chamber is constructed and arranged to allow complete reaction between the ozone and any ethylene in the test gas, prior to exhaustion of the gases from the test chamber.

* * * * *

UNITED STATES PATENT AND TRADEMARK OFFICE
CERTIFICATE OF CORRECTION

PATENT NO. : 6,240,767 B1
APPLICATION NO. : 09/523254
DATED : June 5, 2001
INVENTOR(S) : Bruce Nelson, James Kane and Roy V. Richard It is certified that error appears in the above-identified patent and that said Letters Patent is hereby corrected as shown below:

On the title page, item [73] should read --Assignee: GEO-CENTERS, INC., Newton Centre, Massachusetts--.

Signed and Sealed this

Nineteenth Day of December, 2006

JON W. DUDAS
*Director of the United States Patent and Trademark Office*